United States Patent [19]

Oosten

[11] 4,318,409

[45] Mar. 9, 1982

[54] ELECTROSURGICAL GENERATOR

[75] Inventor: Roger L. Oosten, New Port Richey, Fla.

[73] Assignee: Medical Research Associates, Ltd. #2, South Clearwater, Fla.

[21] Appl. No.: 104,692

[22] Filed: Dec. 17, 1979

[51] Int. Cl.³ .............................................. A61B 17/39
[52] U.S. Cl. ............................ 128/303.14; 128/303.17
[58] Field of Search ...................... 128/303.13, 303.14, 128/303.17, 303.18

[56] References Cited

U.S. PATENT DOCUMENTS

| | | | |
|---|---|---|---|
| 3,699,967 | 10/1972 | Anderson | 128/303.14 |
| 3,801,800 | 4/1974 | Newton | 128/303.14 V |
| 3,885,569 | 5/1975 | Judson | 128/303.14 |
| 4,071,028 | 1/1978 | Perkins | 128/303.14 |
| 4,123,673 | 10/1978 | Gonser | 128/303.13 X |
| 4,154,240 | 5/1979 | Ikuno et al. | 128/303.14 |

Primary Examiner—Lee S. Cohen
Attorney, Agent, or Firm—Gipple & Hale

[57] ABSTRACT

A fixed high frequency oscillator, variable frequency divider, and low frequency timer are provided to produce a high frequency output pulse group which is terminated at different intervals by both the variable frequency divider and the timer. The characteristics of the frequency divider may be varied to produce a number of modes of generator operation, all of which utilize a single high frequency output. The generator includes circuitry for producing a voltage spike as one of the pulses of each output group with a ratio of peak power to RMS power of at least 10:1 in the cut command group and at least 19:1 in the coagulate command group. The spike reionizes the current path through tissue without excessive tissue destruction due to wasted power. A pair of opto-isolated hand-held switches allow the user to select continuously between two preset modes of operation without risking shock.

32 Claims, 13 Drawing Figures

ELECTROSURGICAL GENERATOR

BACKGROUND OF THE INVENTION

This invention relates to an electrosurgical generator, and more specifically to an electrosurgical generator which selectively generates a variety of coagulate signals and cutting signals.

Past electrosurgical generators normally produced a variety of signals, and have controls to adjust signal strength and other parameters of operation. One problem with past electrosurgical generators has been that the multiplicity of controls impaired the treating physician's ability to switch rapidly from one signal mode to another, a particularly crucial problem when medical exigencies require rapid response. Since such controls are most useful when placed within easy reach of operating personnel, isolation from shock hazard is very important, not only for the patient, but also for the physician. Past generators have typically used only a single isolation transformer with the side taps coupled through blocking capacitors to the output terminal. This isolation scheme has often proved inadequate to eliminate the danger of electric shock. For a discussion of the prior art of isolation, see the U.S. Pat. No. 4,094,320 to Newton et al, assigned to Valleylab, Inc.

Furthermore, past electrosurgical generators have produced a simultaneous cutting and coagulating effect, known in the art as a blend signal, by literally blending a cut signal and a coagulate signal. Since significantly different signal levels are required to produce comparable levels of effectiveness between these two signals, past generators have included complex hardware to accomplish an effective literal blending. See, for example, the U.S. Pat. No. 4,154,240 to Ikuno et al.

Incisions created by electrosurgical generators are based on the creation of an ionization path between the closely-spaced electrodes of the electrosurgical scalpel. Past generators have normally utilized high power output levels to maintain an active ionization path, which not only required a massive power supply and generating hardware, but also dissipated waste heat along the incision, and disrupted tissue unnecessarily. A typical prior art electrosurgical incision of the skin would therefore cause a continuous explosive sputtering of the fat layer directly underneath the skin, and the skin incision would heal slowly to produce substantial scar tissue. Users of prior art electrosurgical generators would typically make an initial incision through the skin and fat layer with the traditional knife scalpel in order to avoid this problem.

Some prior art generators have featured a constant-current output amplifier in order to produce a uniform electrosurgical effect over a fairly broad range of tissue impedance. In this regard see U.S. Pat. No. 3,601,126 for an output feedback system to maintain constant output levels. Where differing signal frequencies were used as the basis for different generator output modes, the change in frequency would change the output impedance of the amplifier. In this regard see U.S. Pat. No. 3,699,967, assigned to Valleylab, Inc. Thus, past generators with constant-current output amplifiers were in fact limited to a fairly narrow range of tissue types and incision techniques.

SUMMARY OF THE INVENTION

In accordance with the present invention there is provided a fixed high frequency oscillator, a variable frequency divider, a low frequency oscillator or timer, means for interrupting the fixed high frequency oscillator output signal using both the frequency divider and the timer and means for altering the interruption pattern of the frequency divider in order to produce a pure cut, blend, fulgurate or desiccate output signal. One pulse of each output pulse group is an extremely narrow voltage spike which re-establishes the ionization path through local tissue anomalies such as gristle in normal non-homogenous human tissue. The high ratio of peak power to RMS power in this pulse spike allows re-ionization without harmful dissipation of excess power through tissue. The remaining pulses of each output pulse group are of uniform peak voltage substantially lower than the peak of the previous voltage spike and the output pulse group as a whole produces an incision using minimal electrical power and which will heal rapidly with minimal scar tissue. Repeated re-ionization using the voltage spike makes the present invention especially useful for initial incisions through skin and fat layers without sputtering, which avoids the need for a starter incision made by a knife scalpel.

Because the four modes of operation of the present invention are based on the use of a single fixed high frequency oscillator to generate an output signal, the impedance of the output amplifier is not affected by variation in output frequency. The present invention is therefore more useful than the prior art over a wide variety of application parameters including electrode types, human tissue impedance variation, and differences in incision motions used by treating physicians. Users will find that less practice is required with the present invention than with the prior art in order to learn an effective incision stroke.

The present invention also provides isolation from shock hazard at a plurality of points in the generator. The hand-held control switches are isolated from the command control using a small dedicated power supply and an opto-isolator. The output of the interrupt means is coupled to the input of the main amplifier through a blocking capacitor to block spurious D.C. current from passing to the patient, and various stages of the output amplifier are isolated from one another by isolation transformers. Further, the three taps of the secondary winding of the final output transformer are coupled to output terminals through blocking capacitors also.

DETAILED DESCRIPTION OF THE DRAWINGS

Figure 1:
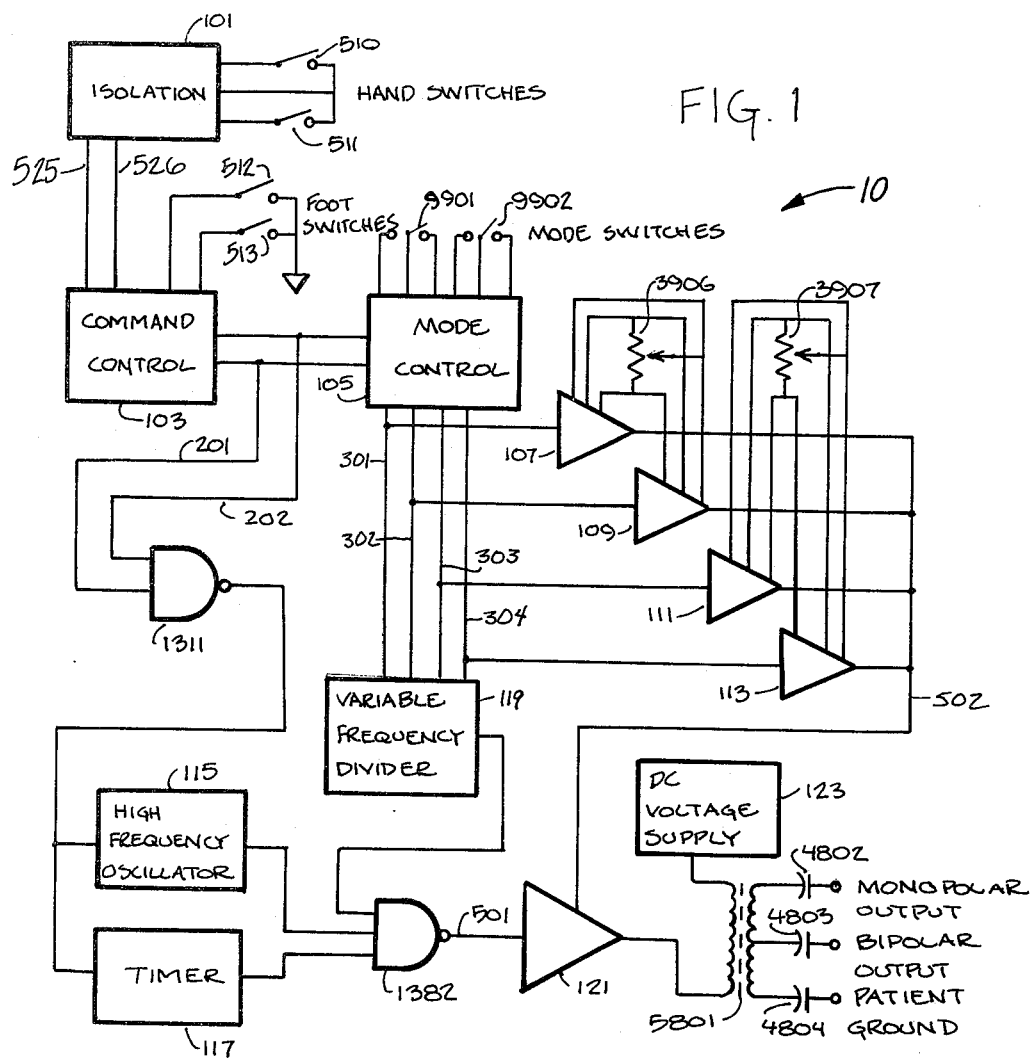
FIG. 1 is a partial block diagram and partial circuit diagram showing one example of the electrosurgical generator according to this invention.

The best mode and preferred embodiment of the invention is shown in FIGS. 1 through 6 and 8 and comprises a signal generating circuit generally indicated at 10 to selectively generate a pure cut signal, a blend signal, a fulgurate signal, or a desiccate signal. These four modes of operation are treated as two command groups: the cut command includes the pure cut and blend modes, while the coagulate command includes the fulgurate and desiccate modes. The treating physician may continuously select either the cut command or the coagulate command using the hand switches 510 and 511 or the foot switches 512 and 513. The hand switches, which are most likely to come into electrical contact with the patient or physician during normal use, are isolated from the bulk of the electric circuit by isolation circuit 101. If both the cut and the coagulate commands are selected simultaneously by the physician, the command control 103 will shut off all functions until the command ambiguity is resolved. Otherwise, the command control 103 activates the line 201 if the cut command is chosen, or line 202 if the coagulate command is chosen.

The command line thus activated will in turn activate one of the two mode switches 9901 or 9902 which are part of the mode control 105. Switch 9901 is enabled by the cut command line 201 and allows the operator to choose between the two cut modes: pure or blend. Switch 9902 is enabled by the coagulate line 202 and allows the operator to choose between the two coagulate modes: desiccate or fulgurate. Since only one of the two command lines are active at any moment, only one of the four mode lines 301, 302, 303 and 304 will be activated by the mode control 105 at any moment.

The active mode line enables one of the four output control amplifiers 107, 109, 111 and 113. These amplifiers produce a voltage controlling the output gain of the main amplifier 121. Amplifiers 107 and 109 control the cut modes output levels and are controlled by potentiometer 3906. Amplifiers 111 and 113 control the output level for the two coagulate functions and are controlled by potentiometer 3907.

Figure 7:
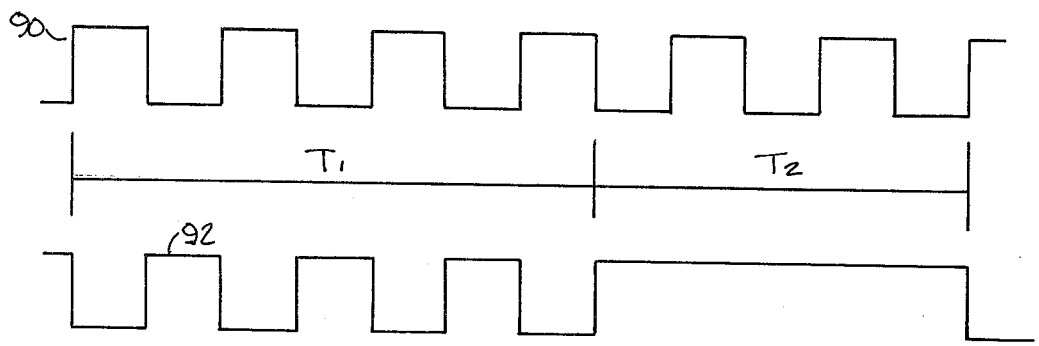
FIG. 7 is a diagram of the wave form of the high frequency oscillator 115 and the variable frequency divider 119 of FIG. 1.

Activation of either of the two command lines 201 or 202 will cause NAND gate 1311 to activate the fixed high frequency oscillator 115 and the timer 117. The output of fixed high frequency oscillator 115, preferably 450 KHz, passes through NAND gate 1382 to reach the main amplifier 121. The variable frequency divider 119 produces the primary modulation of the high frequency signal by counting the output pulses of the fixed high frequency oscillator 115 and periodically interrupting the output of NAND gate 1382. FIG. 7 shows the interruption pattern $T_1+T_2$ of high frequency oscillator output 90 produced by divider 119. The uninterrupted period $T_1$ of NAND gate output determines the duration of the output pulse group and is chosen by the activated mode line, and the repetition period of of interruption $T_1+T_2$ is a fixed multiple of the wavelength of high frequency oscillator output 90. The resulting output waveform of NAND gate 1382 is shown at 92.

The output of NAND gate 1382 is also interrupted periodically by timer 117 to produce a secondary modulation of the high frequency signal. The timer operates at a fixed frequency much lower than that of the fixed high frequency oscillator 115 and the variable frequency divider 119, preferably 5 KHz.

The output of NAND gate 1382 is fed to the input of main amplifier 121. As previously stated the output level of the main amplifier 121 is set by the output of the activated output control amplifier. The main amplifier output draws current from the D.C. voltage source 123 through the primary winding of isolation transformer 5801. The two side taps of the secondary winding of isolation transformer 5801 are connected to capacitor 4802 and 4804, respectively, and the center tap is coupled to capacitor 4803. These capacitors block D.C. current from passing to the patient. The treating physician may choose between bipolar and monopolar output configurations by making appropriate connections between the patient electrodes and the capacitors coupled to the taps of the secondary winding of the transformer.

Figure 8:
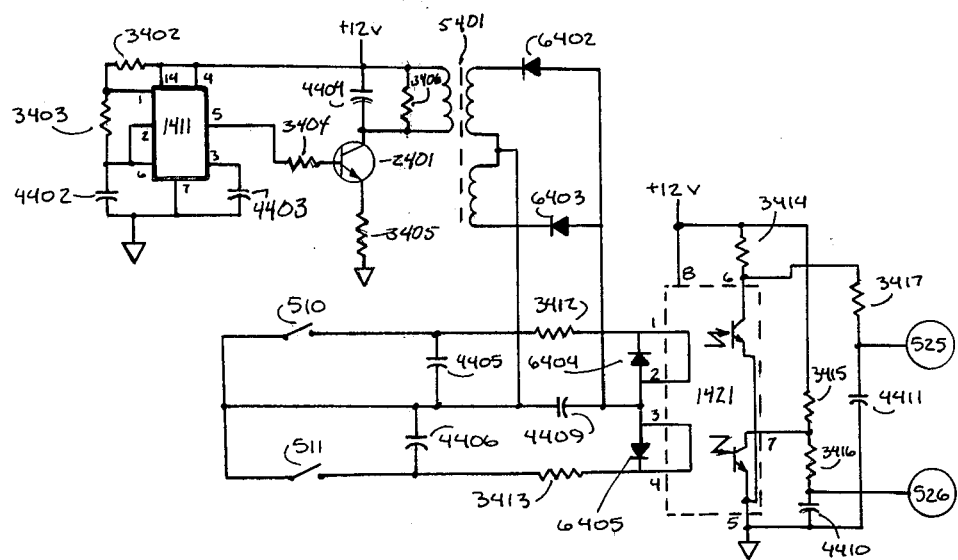
FIG. 8 is a circuit diagram of the isolation 101 of FIG. 1.
Figure 10:
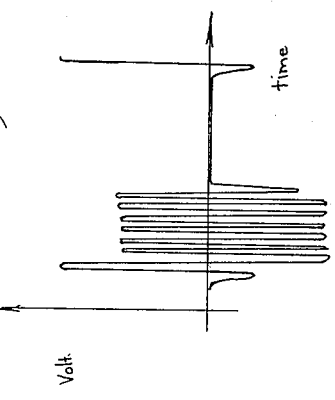
FIG. 10 is a diagram of the output wave form of the electrosurgical generator in blend mode.
Figure 12:
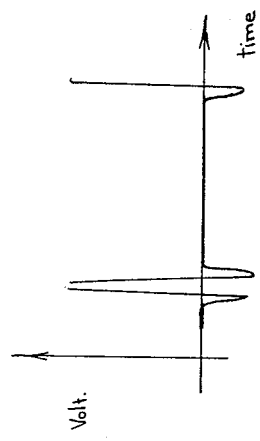
FIG. 12 is a diagram of the output wave form of the electrosurgical generator in fulgurate mode.
Figure 9:
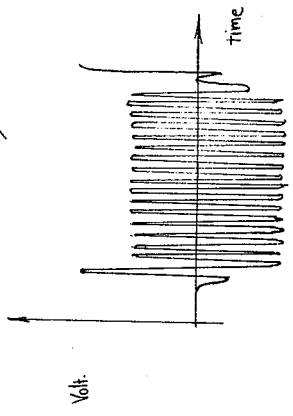
FIG. 9 is a diagram of the output wave form of the generator in pure cut mode.
Figure 11:
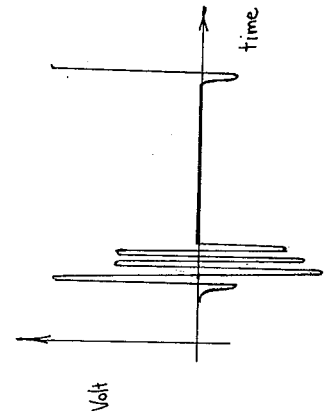
FIG. 11 is a diagram of the output wave form of the electrosurgical generator in desiccate mode.

FIG. 8 illustrates an isolation circuit 101 which isolates and reduces RF leakage between hand-held command switches 510, 511 and the command control 103. The isolation circuit consists of an audio frequency oscillator, preferably running at 23 KHz, which pulses transistor 2401. The oscillator is formed by integrated circuit 1411, typically a type 556 timer with 12 volts supplied to pins 4 and 14. Resistor 3402 connects pins 14 to 1; resistor 3403 connects pin 1 to pins 2 and 6. Capacitor 4402 connects pin 6 to ground, capacitor 4403 connects pin 3 to ground, and pin 7 is grounded directly.

The output of integrated circuit 1411 passes from pin 5 through resistor 3404 to the base of transistor 2401. Resistor 3405 couples the emitter of transistor 2401 to ground, and the collector of transistor 2401 is coupled to the 12 volt supply through capacitor 4404, resistor 3406, and the primary winding of transformer 5401 in parallel. As the oscillator pulses transistor 2401, current is alternately blocked or drawn through the primary winding of transformer 5401. The cathodes of diodes 6402 and 6403 are coupled to the side taps of the secondary winding of transformer 5401. Capacitor 4409 couples the center tap of the secondary winding of transformer 5401 to the anodes of diodes 6402 and 6403. The center tap is further coupled directly to the common line connecting hand switches 510 and 511. Capacitor 4405 couples the center tap of the secondary winding of transformer 5401 to switch 510 and resistor 3412. Switch 510 is connected through resistor 3412 to pin 1 of opto-isolator 1421. Diode 6404 is connected between pins 1 and 2 of opto-isolator 1421; pin 2 is also connected to anodes of diodes 6402 and 6403.

Similarly, capacitor 4406 couples the center tap of the secondary winding of transformer 5401 to switch 511 and resistor 3413. Switch 511 is connected through resistor 3413 to pin 4 of opto-isolator 1421; pin 4 is also connected through diode 6405 to pins 3 and 2 and to the anodes of diodes 6402 and 6403.

Opto-isolator 1421 is supplied with 12 volts at pin 8, and is grounded to the output circuit ground at pin 5.

Pin 6 is the output for switch 510, and is connected through resistor 3414 to pin 8, through resistor 3417 to line 525, and through resistor 3417 and capacitor 4411 in series to pin 5. Pin 7 is the output for switch 511, and is coupled through resistor 3415 to pin 8, through resistor 3416 to line 526, and through resistor 3416 and capacitor 4410 in series to pin 5.

The secondary voltage of the transformer is full wave rectified and filtered to a D.C. voltage by diodes 6402 and 6403 and capacitor 4409. Resistors 3412 and 3413 limit the small amount of D.C. current supplied to the hand switches and the input diodes of opto-isolator 1421. For example, when the cut command group is activated by closing switch 510, current flows through resistor 3412 and pins 1 and 2 of opto-isolator 1421 which causes the output of the opto-isolator 1421 to go low.

Figure 2:
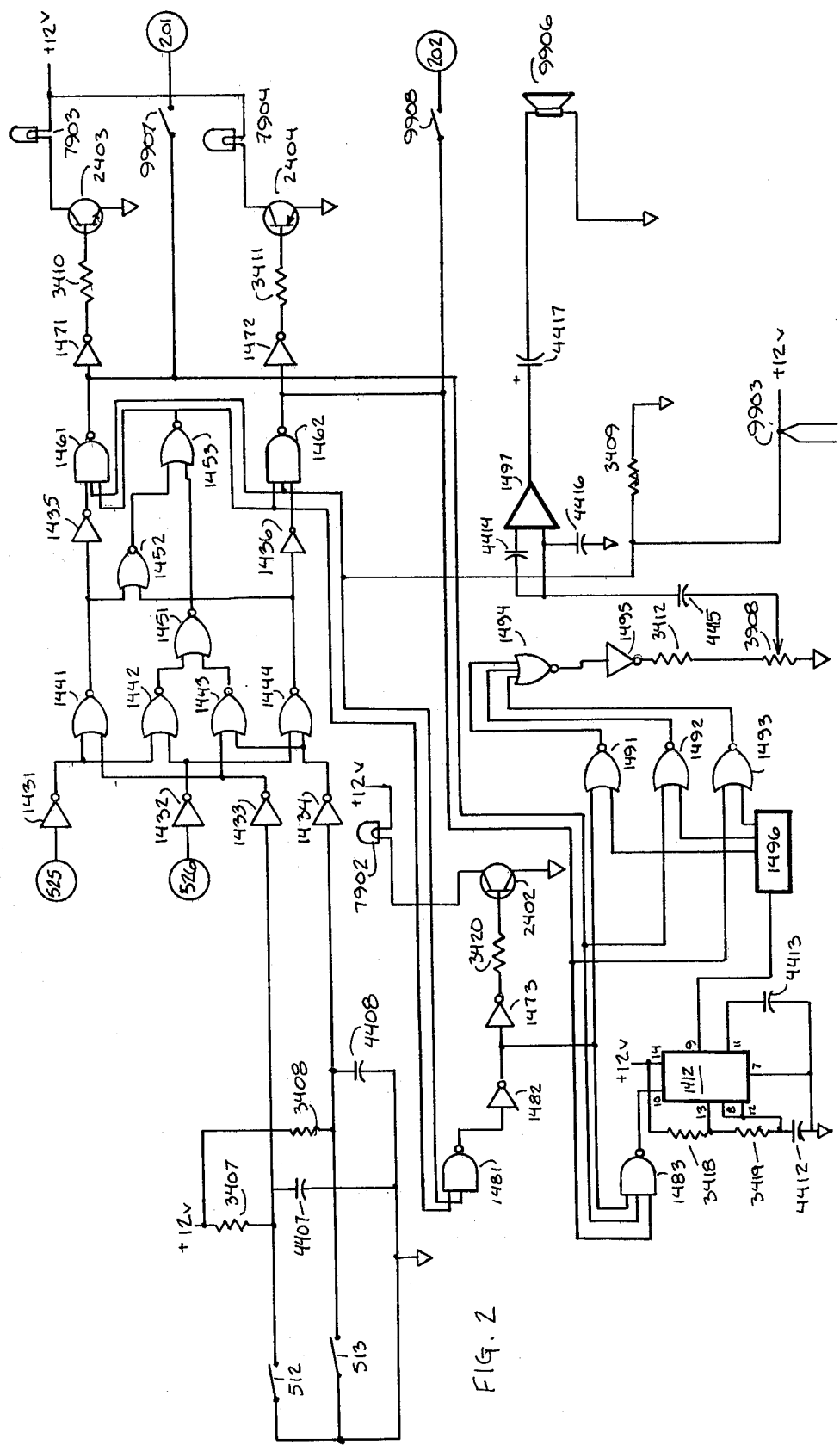
FIG. 2 is a circuit diagram showing the command control 103 of FIG. 1.

Referring now to FIG. 2, the inputs of inverters 1431 and 1432 are connected to the hand switches 510 and 511, respectively, via isolation 101 and lines 525 and 526 respectively. The input of inverter 1433 is coupled through switch 512 and capacitor 4407 in parallel to ground, and through resistor 3407 to a 12 volt supply. Likewise, the input of inverter 1434 is coupled through switch 513 and capacitor 4408 in parallel to ground and through resistor 3408 to a 12 volt supply. Therefore, the inputs of inverters 1433 and 1434 will remain at high value unless a switch is closed, at which time the respective inverter input will go low and its output will go high.

The outputs of inverters 1431 and 1433 are coupled directly to the inputs of NOR gate 1441. Therefore, when either or both of switches 510 and 512 are opened, the output of NOR gate 1441 will be low. The outputs of inverters 1432 and 1434 are coupled directly to the inputs of NOR gate 1444. Therefore, when either or both of switches 511 and 512 are opened, the output of NOR gate 1444 will be low.

The outputs of inverters 1431 and 1432 are also coupled to the inputs of NOR gate 1442. When either or both of switches 510 and 511 are opened, the output of NOR gate 1442 will go low. The output of inverters 1433 and 1434 are coupled to the inputs of NOR gate 1443. When either or both of switches 510 and 511 are opened, the output of NOR gate 1443 will go low. The outputs of NOR gates 1442 and 1443 are coupled to the inputs of NOR gate 1451, and the outputs of NOR gates 1441 and 1444 are coupled to the inputs of NOR gate 1452. The outputs of NOR gates 1451 and 1452 are coupled to the inputs of NOR gate 1453.

The cut command may be indicated by closing either of switches 510 or 512, and the coagulate command may be indicated by closing either of switches 511 or 513. When any two switches are closed indicating conflicting operation modes at the same time, the output of NOR gate 1453 will go low.

The output of NOR gate 1441 is coupled through inverter 1435 to one input of NAND gate 1461. The output of NOR gate 1453 is connected to another input of NAND gate 1461, and the output of thermostat 9903 is coupled to a third input of NAND gate 1461. Thus, when the output of inverter 1435 is high, indicating cut command, and the output of NOR gate 1453 is high, indicating no conflicting command, and the output of thermostat 9903 is high, indicating no heat overload, then the output of NAND gate 1461 will be low activating the command line 201 through switch 9907. If the output of NOR gate 1453 goes low or the output of thermostat 9903 goes low, the output of NAND gate 1461 goes high, deactivating command line 201.

The output of NAND gate 1461 is also coupled through inverter 1471 and resistor 3410 in series to the base of transistor 2403. The emitter of transistor 2403 is grounded and the collector of transistor 2403 is coupled through lamp 7903 to a 12 volt supply. When NAND gate 1461 activates command line 201, the base of transistor 2403 goes high, drawing current through lamp 7903 which lights to indicate cut command group operation to the treating physician.

Similarly, the output of NOR gate 1444 is coupled through inverter 1436 to one input of NAND gate 1462. The output of NOR gate 1453 is connected to another input of NAND gate 1462, and the output of thermostat 9903 is coupled to a third input of NAND gate 1462. When the output of inverter 1436 is high, indicating coagulate command, and the output of NOR gate 1453 is high, indicating no conflicting command, and the output of thermostat 9903 is high, indicating no heat overload, then the output of NAND gate 1462 will be low, activating the command line 202 through switch 9908. If the output of NOR gate 1453 goes low or the output of thermostat 9903 goes low, the output of NAND gate 1462 goes high, deactivating command line 202.

The output of NAND gate 1462 is also coupled through inverter 1472 and resistor 3411 in series to the base of transistor 2404. The emitter of transistor 2404 is grounded and the collector of transistor 2404 is coupled through lamp 7904 to a 12 volt supply. When NAND gate 1462 activates command line 202, the base of transistor 2404 goes high, drawing current through lamp 7904 which lights to indicate coagulate command group operation to the treating physician.

The output of NOR gate 1453 and thermostat 9903 are also coupled to the inputs of NAND gate 1481. The output of NAND gate 1481 is connected through inverters 1482, 1473, and resistor 3420 in series to the base of transistor 2402. The emitter of transistor 2402 is grounded, and the collector of transistor 2402 is connected through lamp 7902 to a 12 volt supply. If either thermostat 9903 or the output of NOR gate 1453 goes low, then the base of transistor 2402 will go high and current will flow through lamp 7902, indicating to the treating physician that the generator has automatically ceased operation.

The outputs of NAND gate 1461 and 1462 and of inverter 1482 are coupled to the inputs of NAND gate 1483. The output of NAND gate 1483 is connected to pin 10 of integrated circuit 1412. If either command line 201 or 202 is activated, or if the generator is automatically shut down, the output of NAND gate 1483 goes high, activating an oscillator formed by integrated circuit 1412 and associated passive elements. Pin 14 of integrated circuit 1412 is connected to a 12 volt supply, and pin 14 is also connected through resistor 3418 to pin 13. Pin 13 is connected through resistor 3419 to pins 8 and 12. Pin 7 is grounded, and is connected through capacitor 4413 to pin 11. Pin 7 is also coupled through capacitor 4412 to pins 8 and 12. The oscillator output is pin 9 of integrated circuit 1412, which is coupled to the input of binary counter 1496.

Binary counter 1496 divides the output frequency of the oscillator by three different fixed factors. Each of three counter outputs are coupled to an input of NOR gates 1491, 1492, and 1493 respectively. The output of inverter 1482 is coupled to the second input of NOR gate 1491, so that when NOR gate 1453 or thermostat 9903 causes a shutdown, the output of NOR gate 1491 will be the inverse of the associated input from the counter 1496. Likewise, command line 201 is coupled to the second input of NOR gate 1492; so that when command line 201 is activated, the output of NOR gate 1492 will be the inverse of the associated input from the counter 1496. Further, command line 202 is coupled to the second input of NOR gate 1493, so that when command line 202 is activated, the output of NOR gate 1493 will be the inverse of the associated input from the counter 1496.

The outputs of NOR gates 1491, 1492, and 1493 are coupled to the inputs of NOR gate 1494. Thus, the output of NOR gate 1494 will be a frequency corresponding to the status of the generator: either cut command, coagulate command, or automatic shutdown. If no command is selected, the output of NOR gate 1494 is fixed at high value.

The output of NOR gate 1494 is coupled through inverter 1495, resistor 3412 and potentiometer 3908 to ground. The wiper of potentiometer 3908 is connected through capacitor 4415 to one input of operational amplifier 1497, which input is connected to ground through capacitor 4416. Capacitor 4415 is also coupled to the second input of operational amplifier 1497 through capacitor 4414. The output of operational amplifier 1497 is coupled to ground through capacitor 4417 and loudspeaker 9906 in series. Therefore, the loudspeaker 9906 produces a tone for audible indication of generator status. The volume of the tone is varied by adjustment of the potentiometer 3908.

Figure 3:
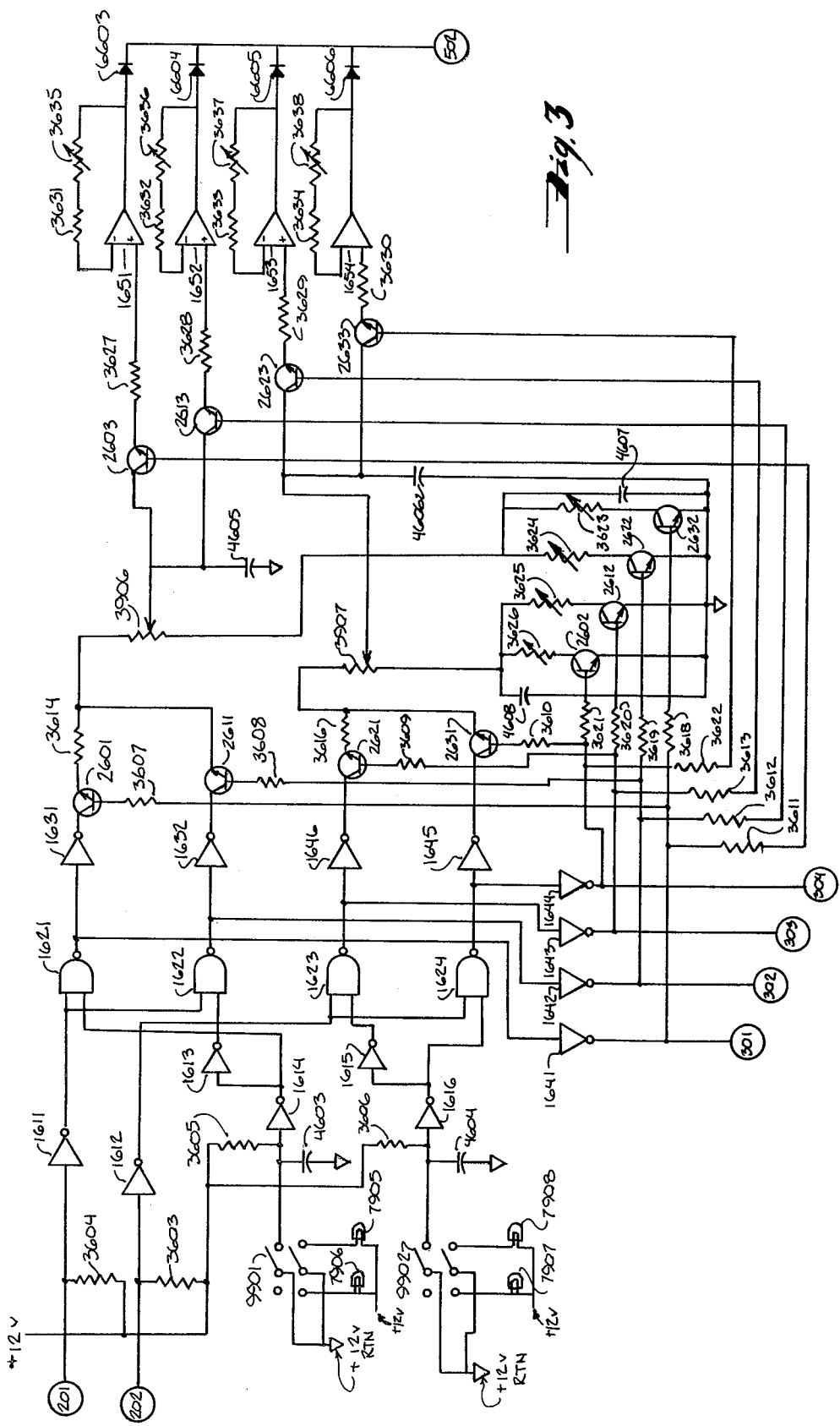
FIG. 3 is a circuit diagram of the mode control 105 and output control amplifier 107, 109, 111 and 113 of FIG. 1.

FIG. 3 shows the mode control 105 and amplifiers 107, 109, 111, and 113. Command line 201 is coupled to the input of inverter 1611. Additionally, a 12 volt source is connected through resistor 3604 to the input of inverter 1611, so that the input of inverter 1611 is normally high value. The output of inverter 1611 is coupled to the input of NAND gate 1621, and to the input of NAND gate 1622.

When command line 201 is activated, the treating physician may select between the pure or blend modes by double pole/double throw switch 9901. Both wipers of switch 9901 are grounded. A 12 volt supply is connected through lamps 7905 and 7906 to the respective contacts for one wiper of switch 9901. Of the remaining two contacts of the second wiper of switch 9901, one contact is coupled to the input of inverter 1614, and the other contact is unconnected. A 12 volt supply is also coupled through resistor 3605 to the input of inverter 1614 and from that point through capacitor 4603 to ground. The output of inverter 1614 is coupled to an input of NAND gate 1621 and also coupled to the input of inverter 1613. The output of inverter 1613 is coupled to an input of NAND gate 1622.

Therefore, when command line 201 is activated (i.e., low value) and one wiper of switch 9901 makes contact with lamp 7905, the output of NAND gate 1621 is low and the output of NAND gate 1622 is high. Also, current is drawn through lamp 7905, indicating by light that the pure mode of operation has been selected. When command line 201 is low and switch 9901 makes contact with lamp 7906, the output of NAND gate 1621 is high and the output of NAND gate 1622 is low. Also, a lamp 7906 is lit, giving a visual indication that the blend mode of operation has been selected.

Similarly, when command line 202 is activated, the treating physician may select between the desiccate or fulgurate operations by double pole/double throw switch 9902. Both wipers of switch 9902 are grounded. A 12 volt supply is connected through lamps 7907 and 7908 to the respective contacts for one wiper of switch 9902. Of the remaining two contacts of the other wiper of switch 9902, one contact is coupled to the input of inverter 1616, and the other contact is unconnected. A 12 volt supply is also coupled through resistor 3606 to the input of inverter 1616 and from that point through capacitor 4604 to ground. The output of inverter 1616 is coupled to the input of NAND gate 1624 and also coupled to the input of inverter 1615. The output of inverter 1615 is coupled to the input of NAND gate 1623.

Therefore, when command line 202 is activated (i.e., low value) and one wiper of switch 9902 makes contact with lamp 7907, the output of NAND gate 1623 is low and the output of NAND gate 1624 is high. Also, current is drawn through lamp 7907, indicating by light that the desiccate mode of operation has been selected. When command line 202 is low and switch 9901 makes contact with lamp 7908, the output of NAND gate 1623 is high and the output of NAND gate 1624 is low. Also, lamp 7907 is lit, giving a visual indication that the fulgurate mode of operation has been selected.

A typical amplifier 107 may be described as follows. The output of NAND gate 1621 is connected to the input of inverter 1631, and the output of inverter 1631 is connected to the collector of transistor 2601. The output of NAND gate 1621 is also coupled to the input of inverter 1641, which supplies base current to the three transistors associated with the pure mode amplifier 107. The output of inverter 1641 is coupled through resistor 3607 to the base of transistor 2601. The output of inverter 1641 is also coupled through resistor 3618 to the base of the transistor 2632. Further, the output of inverter 1641 is coupled through resistor 3611 to the base of transistor 2603. Transistors 2601, 2632, and 2603 operate in switching mode in this circuit; that is, when the output of inverter 1641 is high and current is supplied through the base resistors of the transistors, the collector and emitter of each transistor are shorted. When no base current is supplied, the collector and emitter are disconnected. The output of inverter 1641 also drives mode line 301.

The emitter of transistor 2601 is connected through resistor 3614 to one side of potentiometer 3906. The other side of potentiometer 3906 is connected to resistor 3623 and capacitor 4607 in parallel. Capacitor 4607 is connected to ground. Resistor 3623 is coupled to the collector of transistor 2632. The emitter of transistor 2632 is connected to ground.

The wiper of potentiometer 3906 is connected through capacitor 4605 to ground, and the wiper is also connected to the collector of transistor 2603. The emitter of transistor 2603 is connected through resistor 3627 to the positive input of operational amplifier 1651.

Therefore, when the output of NAND gate 1621 is low indicating the pure mode of operation, the output of inverter 1631 is high. This voltage is connected through transistor 2601 and resistor 3614 to the potentiometer 3906. The voltage across potentiometer 3906 is established by the difference between the voltage supplied by inverter 1631 and the voltage across variable resistor 3623 and transistor 2632. In effect, variable resistor 3623 sets the minimum value of the output power range which may be controlled by potentiometer 3906.

The output of operational amplifier 1651 is connected through variable resistor 3635 and resistor 3631 to the negative input of operational amplifier 1651. This feedback loop establishes the gain of the operational amplifier configuration so that in effect the variable resistor 3635 establishes the maximum limit of the output power range controlled by the setting of potentiometer 3906. The output of operational amplifier 1651 is also connected through diode 6603 to voltage controlled main amplifier 121 via transmission line 502. The output of operational amplifier 1651 easily overcomes the forward bias voltage of diode 6603, but the reverse bias voltage of diode 6603 prevents any of the other three amplifiers which are coupled to line 502 from creating undesired feedback in operational amplifier 1651.

The amplifiers for the three remaining modes of operation of the invention operate in identical fashion.

Figure 4:
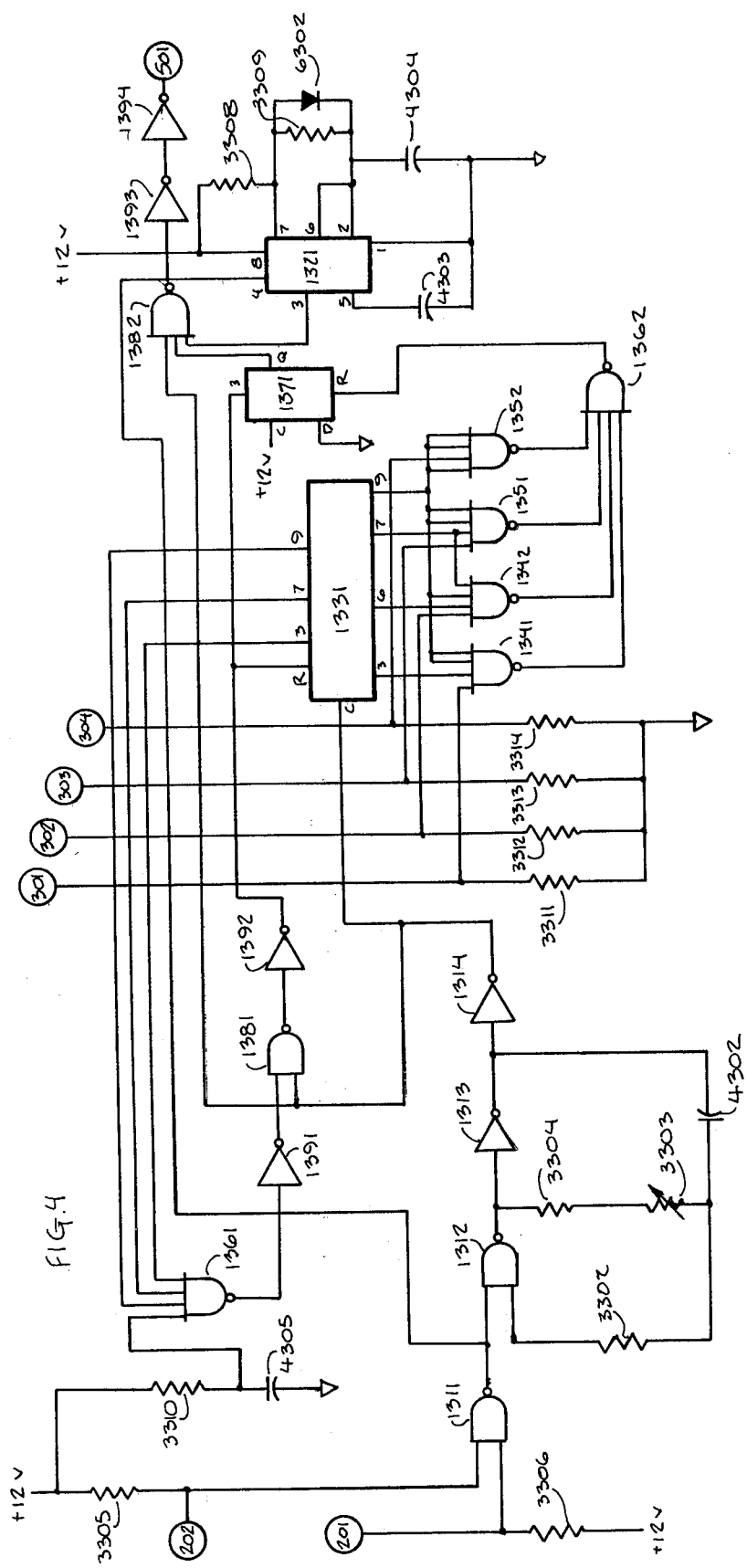
FIG. 4 is a circuit diagram of the high frequency oscillator 115, timer 117, variable frequency divider 119 and NAND gates 1311 and 1382 of FIG. 1.

FIG. 4 shows the high frequency oscillator 115, the variable frequency divider 119, the low frequency oscillator 117 and NAND gates 1311 and 1382.

Command line 201 is connected to one input of NAND gate 1311. A 12 volt supply is also connected through resistor 3306 to that input of NAND gate 1311, so that when command line 201 is not activated, the input will be high. Command line 202 is connected to another input of NAND gate 1311, and the 12 volt supply is also connected through resistor 3305 to this second input of NAND gate 1311 so that when command line 202 is not activated, the second output will also be high. However, if either command line is activated, the output of NAND gate 1311 will go high, activating the fixed high frequency oscillator 115 and the low frequency oscillator 117.

The output of NAND gate 1311 is connected to one input of NAND gate 1312. The output of NAND gate 1312 is coupled to the input of inverter 1313. The output of inverter 1313 is coupled through capacitor 4302 and resistor 3302 in series to the second input of NAND gate 1312. The output of NAND gate 1312 is also coupled through resistor 3304 and variable resistor 3303 in series to the resistor 3302. These elements comprise the fixed high frequency oscillator 115, the frequency of which be initially calibrated and set by adjustment of variable resistor 3303. The output of the oscillator is the output of the inverter 1313, which is coupled to the input of inverter 1314. The output of inverter 1314 is coupled to the input of integrated circuit 1331 and to one input of NAND gate 1382.

The output of NAND gate 1311 is also coupled to pin 4 of integrated circuit 1321. This integrated circuit is preferably a type 555 timer. A 12 volt supply is connected directly to pin 8 and through resistor 3308 to pin 7. Pin 7 is connected through resistor 3309 and diode 6302 in parallel to pins 6 and 2. Pin 2 is connected through capacitor 4304 to ground, pin 1 is connected directly to ground, and pin 5 is connected through capacitor 4303 to ground. Integrated circuit 1321 and associated elements comprise the low-frequency oscillator 117. The output of the low frequency oscillator is pin 3, which is connected to a second input of NAND gate 1382.

Integrated circuit 1331 is preferably a binary counter type 4040. The status of the output pins of integrated circuit 1331 presents a binary representation of the number of pulses of fixed high frequency oscillator 115. The four NAND gates 1341, 1342, 1351, and 1352 vary the counter's function according to the mode selected by the operator, as represented by the status of the four mode lines 301, 302, 303, and 304. The four inputs of NAND gate 1341 are connected to mode line 301 and to pins 3 and 9 (twice) of integrated circuit 1331. The inputs of NAND gate 1342 are connected to the mode line 302 and pins 6, 7, and 9. The inputs of NAND gate 1351 are connected to mode line 303 and to pins 7 and 9 (twice). The inputs of NAND gate 1352 are connected to mode line 304 and to pin 9 (thrice). The output of each of these four NAND gates are connected to the input of NAND gate 1362, and the output of NAND gate 1362 is connected to the reset pin of integrated circuit 1371 which is a set/reset flip-flop preferably of type 4013.

Pins 3, 7, and 9 of integrated circuit 1331 are connected to three inputs of NAND gate 1361. The fourth input of NAND gate 1361 is coupled through resistor 3310 to a 12 volt supply, and through capacitor 4305 to ground. The output of NAND gate 1361 is connected to the input of inverter 1391. The output of inverter 1391 is connected to one input of NAND gate 1381 and the output of inverter 1314 is connected to the second input of NAND gate 1381. The output of NAND gate 1381 is coupled to the input of inverter 1392, and the output of inverter 1392 is coupled to the set pin of integrated 1371 and to the reset pin of the integrated circuit 1331.

The Q output of integrated circuit 1371 is connected to a third input of NAND gate 1382. The C-pin of integrated circuit 1371 is connected to a 12 volt supply and the D-pin of integrated circuit 1371 is connected to ground.

Integrated circuits 1331 and 1371, and circuit elements connected therebetween, comprise the variable frequency divider 119.

Therefore, when the high frequency oscillator is operating, integrated circuit 1331 will count the number of oscillations until the output of inverter 1392 goes high, which occurs when pins 3, 7, and 9 of integrated circuit 1331 are all high. The pulses of fixed high frequency oscillator 115 will pass through NAND gate 1382 and inverters 1393 and 1394 to the main voltage controlled amplifier so long as the outputs of the low frequency oscillator 117 and variable frequency divider 119 are high. The output of variable frequency divider 119, which is the Q output of integrated circuit 1371, will go low after an output pulse group size determined by the integrated circuit 1331 and the NAND gate selected by the activated mode line. Mode line 301, which indicated pure mode, activates NAND gate 1341, which will reset Q after 17 high frequency oscillator pulses. Blend mode line 302 activated NAND gate 1342, which resets Q after 7 pulses of the high frequency oscillator. Desiccate mode line 303 activates NAND gate 1351, which resets Q after 3 pulses. Fulgurate mode line 304 activates NAND gate 1352, which resets Q after 1 pulse. Q remains low and the counter continues to run until 19 pulses are counted, at which time the counter is reset and Q is set to high value. The output waveforms of the pure cut, blend, desiccate, and fulgurate modes are illustrated in FIGS. 9, 10, 11, and 12, respectively.

Figure 5:
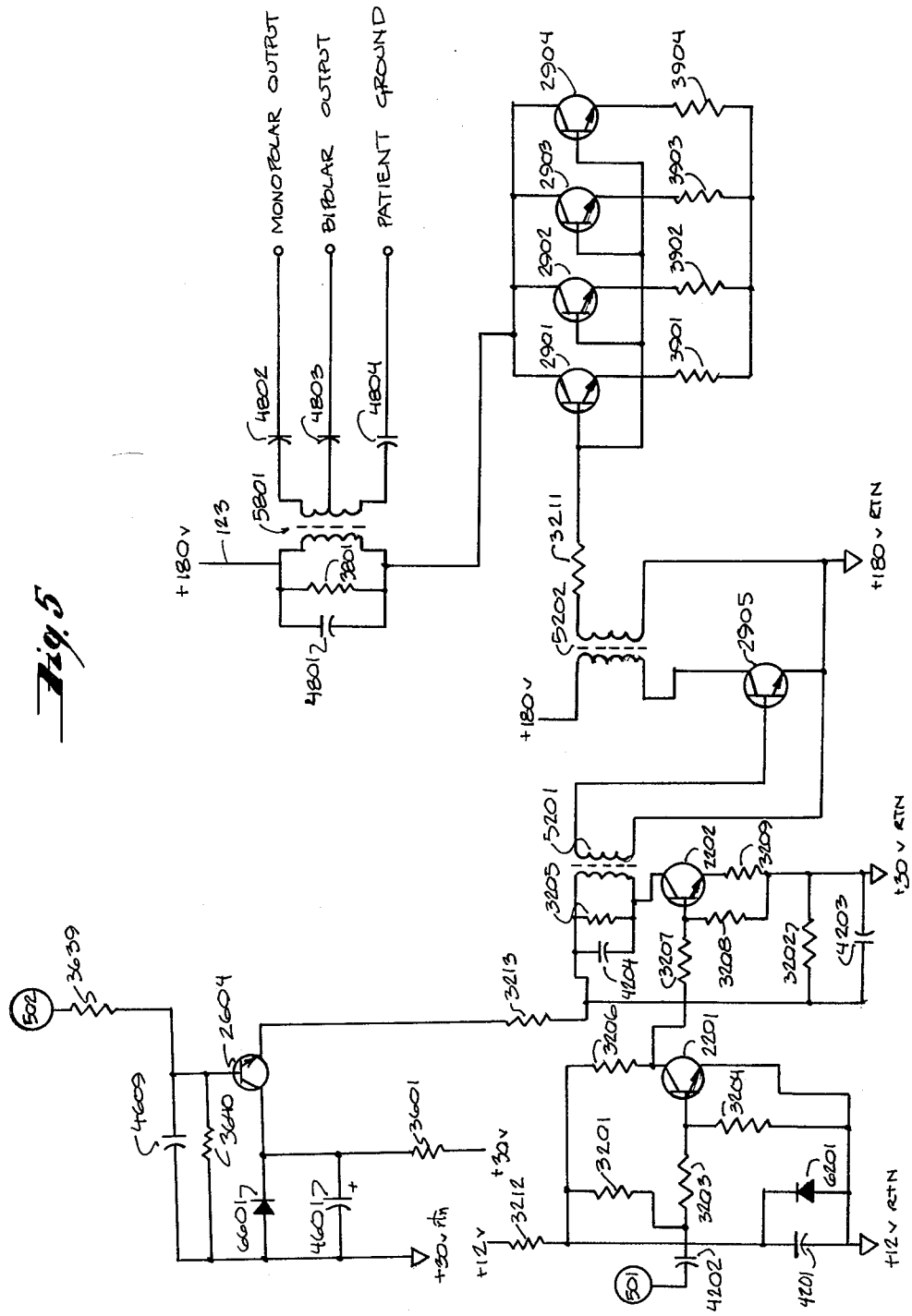
FIG. 5 is a circuit diagram of the voltage controlled main amplifier 121 and transformer 5801 of FIG. 1.

FIG. 5 shows the voltage-controlled main amplifier 121. A 12 volt supply is connected through resistors 3212 and 3206 in series to the collector of transistor 2201. The 12 volt supply is also coupled through resistors 3212, 3201, and 3203 in series to the base of transistor 2201. The base of transistor 2201 is also connected through resistor 3204 to a 12 volt supply return bus. The 12 volt supply is also connected through resistor 3212 to capacitor 4201 in parallel with zener diode 6201, and this capacitor and zener diode are connected to the 12 volt return bus.

The output of NAND gate 1382 is connected through inverters 1393 and 1394 to line 501. Line 501 is coupled through capacitor 4202 and resistor 3203 in series to the base of transistor 2201. Capacitor 4202 blocks spurious DC current from reaching the base of transistor 2201 and passing through main amplifier 121 to the patient. The emitter of transistor 2201 is connected directly to the 12 volt return bus.

The output amplifiers 107, 109, 111, and 113 are connected through line 502 and resistor 3639 in series to the base of transistor 2604. The base of transistor 2604 is also coupled through capacitor 4609 and resistor 3640 connected in parallel to the 30 volt return bus. The collector of transistor 2604 is connected through zener diode 6601 in parallel with capacitor 4601 to the 30 volt return bus, and the collector of transistor 2604 is also connected through resistor 3601 to the 30 volt supply.

The collector of transistor 2201 is connected through resistor 3207 to the base of transistor 2202, and the base of transistor 2202 is also connected through resistor 3208 to the 30 volt return bus. The emitter of transistor 2202 is connected through resistor 3209 to the 30 volt return bus also.

The emitter of transistor 2604 is connected to the gain control stage of the voltage-controlled main amplifier 121. The emitter is coupled through resistor 3213 to capacitor 4203 in parallel with resistor 3202 to the 30 volt supply return bus. The emitter of transistor 2604 is also connected through resistor 3213 to capacitor 4204, resistor 3205, and the primary winding of isolation transformer 5201 in parallel, and through these elements to the collector of transistor 2202.

Capacitor 4204, resistor 3205, and transformer 5201 form a parallel resonant circuit which produces the voltage spike of each output pulse group. While FIGS. 9 through 12 show the voltage spike at the beginning of the output pulse group, the voltage spike can be placed anywhere in the pulse group. Any of the pulses in the pulse group having a high voltage can ionize the current path provided on the current drive portion if the time lag is not excessive. Subsequent pulses of the group or a following group establish a signal frequency outside the resonant frequency range of the resonant circuit to produce lower voltage across the secondary winding of transformer 5201 than does the spike pulse of each group.

Thus, the voltage spike of each output pulse group achieves a high ratio of peak power to RMS power, which ratio will be referred to hereinafter as crest factor ratio. The crest factor ratio obtained in the present invention for the pure cut mode ranges from 10:1 to 11:1; blend mode 11:1 to 13:1; desiccate mode 19:1 to 24:1; and fulgurate mode 20:1 to 25:1. The coagulate command group of the invention thus attains a crest factor ratio of at least 19:1. A high crest factor ratio is desirable as an efficient cause of ionization without excessive tissue heating. The best crest factor ratio known to be achieved in the prior art is 12:1 to 13:1 for the coagulate command group including the fulgurate and desiccate modes by the device described in U.S. Pat. No. 3,699,967.

One side tap of the secondary winding of transformer 5201 is connected to the base of transistor 2905, and the other side tap is connected to the 180 volt return bus. The emitter of transistor 2905 is also connected to the 180 volt return bus. The collector of transistor 2905 is connected through the primary winding of isolation transformer 5202 to the 180 volt supply. One side tap of the secondary winding of transformer 5202 is connected to the 180 volt return bus, and the other side tap is connected through resistor 3211 to the constantcurrent amplifier stage of the voltage-controlled main amplifier 121. Resistor 3211 is connected to the bases of transistors 2901, 2902, 2903, and 2904. The emitters of transistors 2901, 2902, 2903, and 2904 are coupled to one another through resistors 3901, 3902, 3903, and 3904, respectively. Transistors 2901, 2902, 2903 and 2904 form an output stage functioning as a constant-current amplifier through a load ranging from 25 to 2000 ohms, which is typically within the range of human tissue resistance to electrosurgical current. The collectors of transistors 2901, 2902, 2903 and 2904 are coupled to one another and through the primary winding of transformer 5801, resistor 3801, and capacitor 4801 in parallel to the 180 volt supply. One side tap of the secondary winding of transformer 5801 is connected through capacitor 4802 to the monopolar output terminal of the electrosurgical generator. Another side tap is connected through capacitor 4804 to the patient return terminal of the electrosurgical generator. The center tap of transformer 5801 is connected through capacitor 4803 to the bipolar output terminal of the electrosurgical generator.

Figure 6:
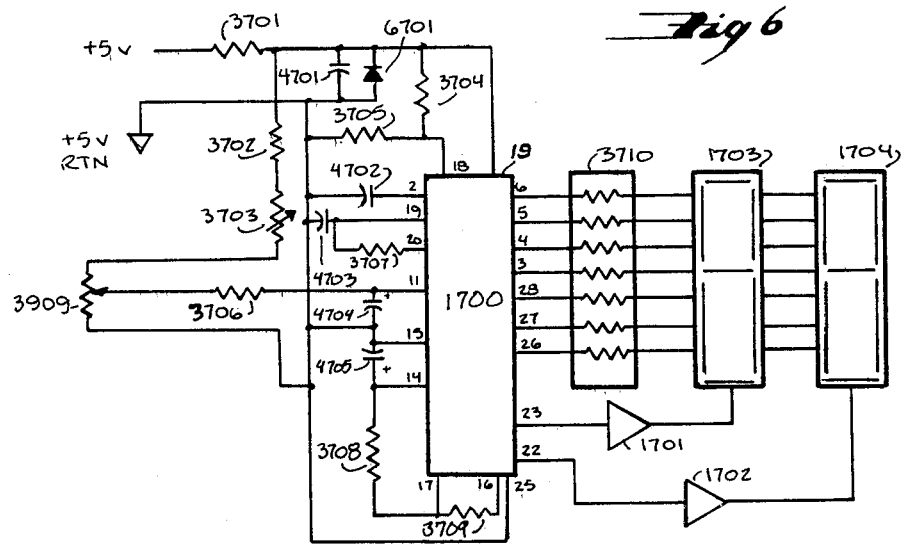
FIG. 6 is a circuit diagram of a digital display of the output level of the output control amplifiers of FIG. 3.

FIG. 6 shows a display device for digital display of the output level of the electrosurgical generator. In the preferred form of the invention, two such displays are included, one for each of the two command groups. Potentiometer 3909 of the first such display device is ganged to potentiometer 3906 for the cut command group, and potentiometer 3909 of the second such device is ganged to potentiometer 3907 for the coagulate command group.

A 5 volt supply is connected through resistors 3701 and 3702 and variable resistor 3703 in series to the potentiometer 3909, and through the potentiometer to the 5 volt return bus. The wiper of potentiometer 3909 is connected through resistor 3706 to pin 11 of integrated circuit 1700. This integrated circuit is preferably a type ADD 3501 CCN analog-to-digital converter. The 5 volt supply is also connected through resistor 3701 to pins 1 and 9 of integrated circuit 1700. Pins 1 and 9 are connected through resistor 3704 to pin 18, and pin 18 is connected through resistor 3705 to the 5 volt return bus. Pin 2 is connected through capacitor 4702 to the 5 volt return bus, pin 19 is connected through resistor 3707 to pin 20, and pin 19 is also connected through capacitor 4703 to the 5 volt return bus. Pin 11 is connected through capacitor 4704 to pin 15, and pin 15 is connected to the 5 volt return bus. Pin 14 is connected through capacitor 4705 to the 5 volt return bus, and pin 14 is also coupled through resistor 3708 to pin 17. Pin 17 is connected through resistor 3709 to pin 16. Pin 25 is coupled directly to the 5 volt return bus.

The output pins of integrated circuit 1700 are pins 6, 5, 4, 3, 28, 27, and 26. These pins are connected through resistor pack 3710 to the segment pins of the 7-segment displays 1703 and 1704 in parallel. Pin 23 of the integrated circuit 1700 is connected to the input of inverter 1701, and the output of inverter 1701 is connected to the drive pin of display 1703. Pin 22 of integrated 1700 is connected to the input of inverter 1702, and the output of inverter 1702 is connected to the drive pin of display 1704.

Figure 13:
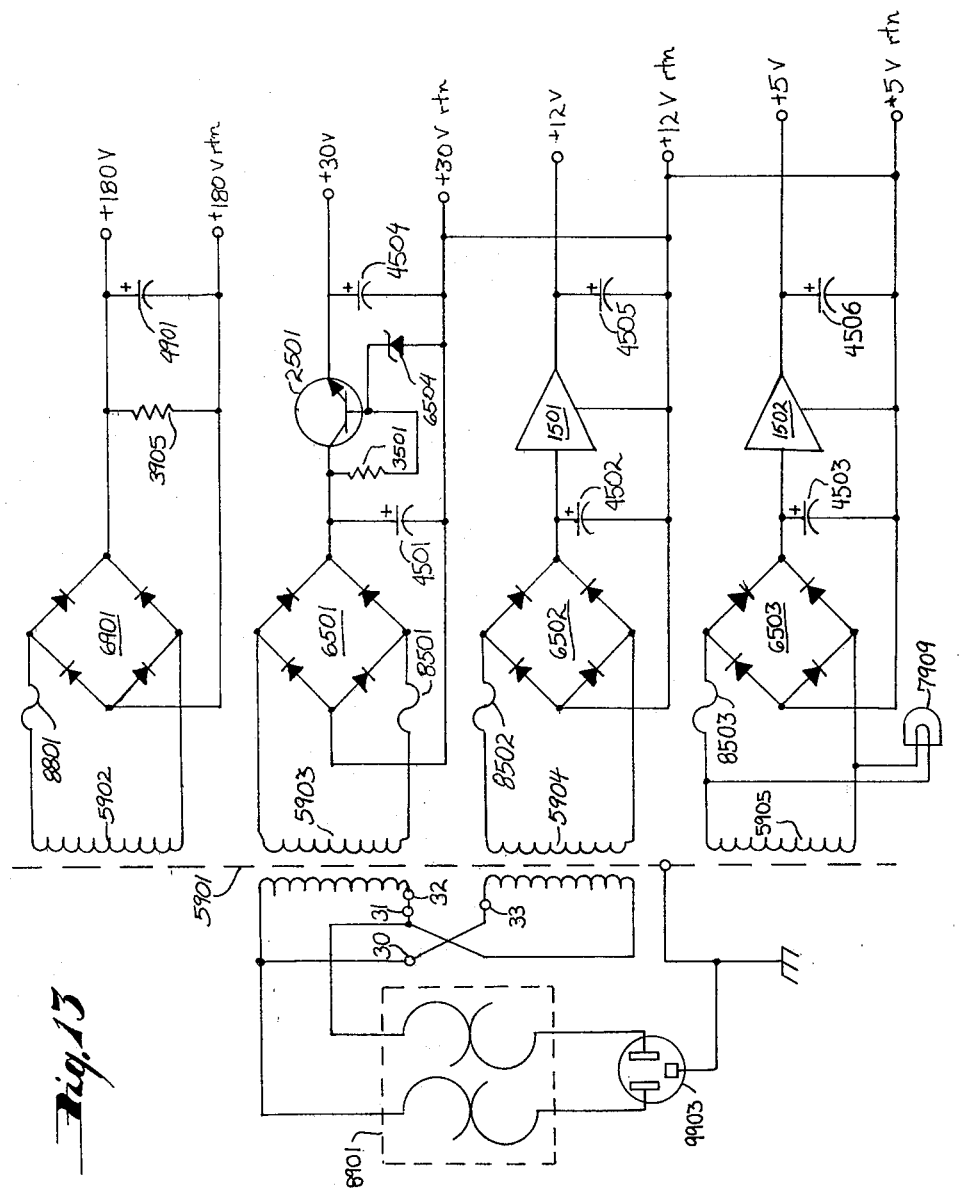
FIG. 13 is a circuit diagram for a power supply for the electrosurgical generator.

FIG. 13 shows a power supply circuit for the electrosurgical generator. The power supply is designed to be supplied with wall current through standard 3-wire plug 9903. The ground pin of plug 9903 is coupled to the core of power transformer 5901, and the two power pins of plug 9903 are connected through the dual-pole circuit breaker 8901 to are side taps of the primary winding of the power transformer 5901. The primary winding is shown wired to accept 110-volt input; however, it may be rewired to accept 220-volt input by breaking the connections at points 30 and 31 and making a connection between points 32 and 33.

Transformer 5901 has four secondary wirings. One side tap of secondary 5902 is coupled directly to one input of full-wave bridge rectifier 6901, and the other side tap is coupled through fuse 8801 to the second input of bridge 6901. The negative output of bridge 6901 is coupled through resistor 3905 and capacitor 4901 in parallel to the positive output of bridge 6901. The positive output of bridge 6901 supplies 180 volts direct current, and the negative output is the return line for this voltage.

One side tap of the secondary 5903 is connected directly to one input of full-wave bridge rectifier 6501, and the other side tap of the secondary is coupled through fuse 8501 to the second input to bridge 6501. The positive output of bridge 6501 is coupled through capacitor 4501 to the negative output of the bridge, and the positive output is also coupled through resistor 3501 to the base of the transistor 2501. The positive output of bridge 6501 is also coupled directly to the collector of transistor 2501. The base of transistor 2501 is coupled through zener 6504 to the negative output of bridge 6501, and the emitter of transistor 2501 is coupled through capacitor 4504 to the negative output. The emitter of transistor 3501 provides 30 volts direct current, which is returned to the negative output of bridge 6501.

One side tap of secondary 5904 is connected through fuse 8502 to one input of full-wave bridge rectifier 6502, and the other side tap of the secondary is connected directly to the second input of bridge 6502. The positive output of bridge 6502 is coupled directly to the input of voltage regulator 1501, and through capacitor 4502 to the negative output of bridge 6502. The ground of voltage regulator 1501 is coupled directly to the negative output of the bridge, and the positive output of the voltage regulator is coupled through capacitor 4505 to the negative output of the bridge. The positive output of voltage regulator 1501 provides 12 volts direct current, which may be returned to the negative input of bridge 6502.

One side tap of the secondary 5905 is connected through fuse 8503 to one input of full-wave bridge rectifier 6503, and the other side tap of the secondary is coupled directly to the second input of bridge 6503. The positive output of bridge 6503 is coupled directly to the input of voltage regulator 1502, and through capacitor 4503 to the negative output of bridge 6503. The ground of voltage regulator 1502 is coupled directly to the negative output to the bridge, and the positive output of voltage regulator 1502 is coupled through capacitor 4506 to the negative output of the bridge. The positive output of the voltage regulator supplies 5 volts direct current, which may be returned to the negative output of the bridge.

The negative output of the bridges 6501, 6502, and 6503 are coupled directly to one another. The side taps of secondary 5905 are coupled through lamp 7909 to give indication of circuit breaker status.

In a working embodiment of this invention, the following components were utilized. It should be appreciated however, that the list of components is for illustration only and the invention is not meant to be limited thereto.

Integrated Circuits

Type 4023 three-input NAND gates: 1461, 1462, 1481, 1482, 1483
Type 4012 quad input NAND gates: 1341, 1342, 1351, 1361, 1362, 1382
Type 4049 inverters: 1391, 1392, 1393, 1431, 1432, 1434, 1435, 1436, 1471, 1472, 1473, 1611, 1612, 1613, 1614, 1615, 1616, 1631, 1632, 1633, 1634, 1641, 1642, 1643, 1644, 1645, 1646
Type 4011 NAND gates: 1311, 1312, 1313, 1314, 1621, 1622, 1623, 1624
Type 4001 NOR gates: 1441, 1442, 1443, 1444, 1451, 1452, 1453, 1491, 1493, 1492
Type 55 timers: 1321
Type 556 timers: 1411, 1412
Type HCPL 2531 opto-isolators: 1421
Type 4025 three-input NOR gates: 1494, 1495
Type 4040 binary counters: 1331, 1496
Type 3900 operational amplifiers: 1651, 1652, 1653, 1654
Type 380N audio amplifiers: 1497
Type 4013 flip-flops: 1371
Type 75492 invertersL 1701, 1702
Type ADD 3501 CCN analog-to-digital converters: 1700
7-Segment displays: 1703, 1704
Type LM340T12 voltage regulator: 1501
Type LM340T5 voltage regulator: 1502

Capacitors 10 uF, 35 v: 4201, 4301, 4409, 4417, 4702
0.1 uF, 50 v: 4202, 4415, 4416, 4603, 4604, 4605, 4606, 4607, 4608, 4609
50 uF, 50 v: 4203, 4401, 4504, 4505, 4506
200 pF, 500 v: 4204
0.01 uF, 100 v: 4303, 4304, 4403 4404, 4405, 4406, 4407, 4408, 4410, 4411, 4412, 4413, 4418, 4419
100 pF, 200 v: 4302
0.1 uF, 35 v: 4306
0.001 uF, 200 v: 4414
47 uF, 20 v: 4701
220 pF, 200 v: 4703
0.47 uF, 35 v: 4704, 4705
22000 pF, 500 v: 4801
0.01 uF, 3000 v: 4802, 4803, 4804
500 mF: 4901
10 uF, 50 v: 4601, 4602
150 uF, 50 v: 4501
500 uF, 35 v: 4502, 4503

Transistors

2N222A: 2201, 2401
2N6044: 2202, 2501, 2604
IR 519: 2905
MPQ2222: 2402, 2403, 2404, 2601, 2602, 2603, 2611, 2621, 2631, 2612, 2622, 2632, 2613, 2623, 2633
DTS 430: 2901, 2902, 2903, 2904

Resistors (all ¼ watt, 5% unless specified otherwise)

22K: 3201, 3302, 3310
10K: 3202, 3208, 3305, 3306, 3311, 3312, 3313, 3314, 3407, 3408, 3409, 3414, 3415, 3418, 3603, 3604, 3605, 3606, 3607, 2608, 2609, 3610, 3611, 3612, 3613, 3614, 3616, 3618, 3619, 3620, 2621, 2622, 3704
1K: 3203, 3206, 3404, 3410, 3411, 3412, 3413, 3416, 3417, 3420, 3420, 3639
47K: 3204, 3905
680: 3205, 3406
47: 3207
10: 3209, 3210 (1 watt)
20: 3211 (10 watt)
27: 3213, 3213, 3601
15: 3301 (½ watt), 3401 (½ watt), 3405 (½ watt), 3602 (½ watt), 3701
2.7K: 3304
330K: 3308
220K: 3309, 3627, 3628, 3629, 3630, 3634, 3709
6.8K: 3402, 3707
27K: 3403, 3419
2.2K: 3501
100K: 3631, 3632, 3633, 3706, 3708
33K: 3702
8.2K: 3705
100: 3710
500: 3801 (10 watt)
1 (25 watt): 3901, 3902, 3903, 3904

Diodes:

Zener 1N4744A: 6201
Zener 1N4751A: 6504
1N4001: 6302, 6402, 6403, 6404, 6405, 6603, 6604, 6605, 6606
Zener 1N4735A: 6701
Zener 1N4752A: 6602
Full wave bridge rectifier, 2 amp: 6501, 6502, 6503
Full wave bridge rectifier, 12 amp: 6901

Fuses:

1 amp: 8501, 8502
½ amp: 8503
8 amp: 8801
7.5 amp circuit breaker, dual pole: 8901

In preparation for operation of the invention, a return electrode, preferably of relative large area, should be applied to the patient and connected to the patient return terminal of the electrosurgical generator output. Also, the electrode scalpel should be plugged into the monopolar output or the monopolar and bipolar outputs as may be appropriate for the particular electrode scalpel configuration.

Operation of the invention is begun by turning on circuit breaker 8901 to provide power to the power supply of the electrosurgical generator. Mode switches 9901 and 9902 are then adjusted to preset the modes to be activated during the course of surgery by selection of either the cut command or the coagulate command. The power levels to be applied during each mode of operation are then set by adjusting the potentiometers 3906 and 3907 which settings can be read from the dual digital display systems.

To begin surgery, either of switches 510 or 512 may be closed to activate the cut command group, or either of switches 511 or 513 may be closed to activate the coagulate command group. Output to the electrode scalpel can be interrupted at any time without adjusting the circuit breaker 8901 by opening the switch which has been closed or by closing a switch activating the opposite command group. In the latter case, or if the thermostat 9903 detects overheating of the output transistors, then the command control automatically activates the appropriate lamp and changes the output frequency of the tone generator to indicate an automatic shutdown of operation. If automatic shutdown is not encountered, then the command control activates the command line corresponding to the command switch which has been closed.

In response to the activation of the command line, both the high-frequency oscillator 115 and the timer 117 begin operation. Also, the mode control 105 activates a mode line within the activated command group corresponding to the preset status of switches 9901 or 9902. The activated mode line in turn activates a particular division function of the variable frequency divider 119 and a corresponding one of the four output level amplifiers, 107, 109, 111, or 113. The activated output level amplifier emits a signal corresponding to the adjustment already made to potentiometers 3906 or 3907.

The outputs of the high-frequency oscillator 115, the timer 117, and the variable frequency divider 119 are fed to NAND gate 1382. The output of high frequency oscillator 115 is interrupted by the variable frequency divider 119 to produce a signal causing tissue destruction corresponding to the mode selected by the command switch and the mode switch. The timer 117 interrupts the output of high frequency oscillator 115 to provide a duty cycle of operation for protection of power supplies and output transistors. The output of NAND gate 1382 is then amplified by main amplifier 121, the gain of which is set by the activated output level amplifier. The voltage across the primary winding of output transformer 5801 is equal to the level of the D.C. voltage supply 123 minus the output signal of amplifier 121. The current generated through the secondary winding of output transformer 5801 passes through the blocking capacitor 4802 to the electrode scalpel and then may be returned either through the patient return and the blocking capacitor 4804 coupled thereto or to the bipolar output terminal and the blocking capacitor 4803 coupled thereto.

During the surgical procedure, should the physician wish to switch between modes of operation within a command group, only the appropriate mode switch 9901 or 9902 need be manipulated. If one command group is deactivated and the other is started, then the mode control automatically activates the appropriate mode line corresponding to the preset mode switch 9901 or 9902. The power levels of the output may also be continually adjusted by manipulating potentiometers 3906 or 3907.

In the foregoing description the invention has been described with reference to a particular embodiments although it is to be understood that the specific details shown are merely illustrative and that the invention may be carried out in other ways without departing from the true spirit and scope of the following claims.

What is claimed:

1. A generator for electrosurgery comprising first and second command switches for selecting command status of operation, a command control means coupled to said first and second command switches for preventing simultaneous use of said first and second command switches, a first mode switch for selecting the mode of operation when the first command switch is activated, a second mode switch for selecting the mode of operation when the second command switch is activated, a mode control means coupled to said first and second mode switches for determining the mode of operation indicated by said first and second command switches and said first and second mode switches, said command control means being coupled to said mode control means by first and second command lines, first, second, third and fourth voltage amplifiers, said amplifiers being coupled to said mode control means so that one of said amplifiers corresponding to the mode of operation indicated by said first and second mode switches and said first and second command switches is activated by said mode control means, a first NAND gate having two inputs, the two inputs of said first NAND gate being coupled respectively to the said first and second command lines, high frequency oscillator means and low frequency oscillator means coupled to the output of said first NAND gate so that said high frequency oscillator means and low frequency oscillator means are activated when either command line is activated, a three-input NAND gate, the output of said low frequency oscillator means being coupled to a first input of said three-input NAND gate, the output of said high frequency oscillator means being coupled to a second input of said three-input NAND gate, a variable frequency divider means, the output of said high frequency oscillator means also being coupled to said variable frequency divider means, said variable frequency divider means also being coupled to said mode control means, the output of said variable frequency divider means being a first interrupt signal comprised of a high voltage portion and a low voltage portion, the wavelength of said first interrupt signal being an integer multiple of the wavelength of the output of said high frequency oscillator means, the ratio of the length of said high voltage portion to the length of said low voltage portion being altered by said variable frequency divider means according to the mode of operation indicated by said first and second mode switches and said first and second command switches, the output of said variable frequency divider means being coupled to the third input of said three-input NAND gate, a voltage-controlled main amplifier means, the output of said three-input NAND gate being coupled to the input of said voltage-controlled main amplifier means, said voltage-controlled main amplifier means including means for selectively increasing the amplitude of the initial pulse of each group of pulses from said three-input NAND gate, said voltage-controlled main amplifier means being coupled to said first, second, third and fourth amplifiers so that said amplifiers control the output level of said voltage-controlled main amplifier means, and a D.C. voltage supply and an isolation transformer means, the output of said voltage-controlled main amplifier means being coupled through the primary winding of said isolation transformer means to said D.C. voltage supply, the secondary winding of said isolation transformer means providing isolated monopolar and bipolar electrosurgical voltage output.

2. The apparatus as claimed in 1 including a plurality of gain control means coupled to each of said first, second, third, and fourth amplifiers for adjustment of the output voltage of said amplifiers.

3. The apparatus as claimed in claim 2 in which said first and second amplifiers share one of said gain control means, and said third and fourth amplifiers share a second of said gain control means.

4. The apparatus as claimed in claim 1 wherein each of said first and second command switches comprises a plurality of switches connected in parallel.

5. The apparatus as claimed in claim 1 including isolation means comprising a second D.C. power supply and an opto-isolator, each of said first and second command switches being isolated from said command control means by said isolation means.

6. The apparatus as claimed in claim 1 wherein said voltage-controlled main amplifier means includes an output stage, said output stage comprising a constant-current amplifier.

7. The apparatus as claimed in claim 6 wherein said output stage functions as a constant-current amplifier over a human tissue impedance range of 25 to 2000 ohms.

8. The apparatus as claimed in claim 1 including first and second display means for displaying the power output level corresponding to each of said first and second command switches.

9. The apparatus as claimed in claim 1 wherein said initial pulse of each group of pulses has a ratio of peak power to RMS power in the range of 10:1 to 25:1.

10. The apparatus as claimed in claim 6 wherein the input of said output stage includes an isolation transformer.

11. The apparatus as claimed in claim 1 wherein said means for selectively increasing the amplitude of the initial pulse of each group of pulses is a resonant circuit, said resonant circuit comprising a resistor, capacitor and transformer coupled in parallel, said circuit being tuned to a resonant frequency not equal to the frequency of said high-frequency oscillator means.

12. A multiple-mode electrosurgical generator for producing a plurality of modes of tissue transformation by electrosurgery, said modes being grouped into two command groups; said generator comprising command control means for selection of one of said two command groups and for preventing simultaneous selection of said two command groups; mode control means for presetting the mode within each of said two command groups to be activated by said command control means; high frequency oscillator means and low frequency oscillator means; means for activating said high frequency oscillator means and said low frequency oscillator means when either of said command groups is activated by said control means; variable frequency divider means, the output of said high frequency oscillator means being coupled to said variable frequency divider means, said variable frequency divider means being coupled to said mode control means, said variable frequency divider means producing an interrupt signal as a function of the output of said high frequency oscillator means and of the mode of operation preset by said mode control means and activated by said command control means; amplifier means for amplifying the output of said high-frequency oscillator means; interrupt means having a plurality of inputs, the inputs of said interrupt means being coupled to the output of said high-frequency oscillator means, said low-frequency oscillator means, and said variable frequency divider means, respectively, the output of said interrupt means being coupled to the input of said amplifier means, said interrupt means interrupting the output of said high-frequency oscillator means as a function of the output of said low-frequency oscillator means and of said interrupt signal to form output pulse groups of the output of said high-frequency oscillator means; gain control means for varying the output gain of said amplifier means; and output isolation means coupled to the output of said amplifier means, said output isolation means providing isolated bipolar and monopolar electrosurgical voltage.

13. The apparatus as claimed in claim 12 including command selection means comprising two command switches, said command selection means being coupled to said command control means.

14. The apparatus of claim 13 including command isolation means interposed between said command selection means and said command control means, said isolation means isolating said command selection means from said command control means.

15. The apparatus of claim 14 wherein said command isolation means comprises opto-isolator means having an input stage and an output stage, said opto-isolator means preventing passage of current from said command control means to said command selection means, and power supply means to supply power to said input stage of said opto-isolator means.

16. The apparatus of claim 12 wherein said means for activating said high frequency oscillator means and said low frequency oscillator means comprises a NAND gate.

17. The apparatus of claim 12 wherein said interrupt means comprises a NAND gate.

18. The apparatus of claim 12 wherein said gain control means comprises a potentiometer.

19. The apparatus of claim 12 wherein said amplifier means comprises a voltage-controlled main amplifier.

20. The apparatus of claim 19 wherein said gain control means comprises a plurality of mode amplifiers, the number of said mode amplifiers being equal to the number of said modes, and each amplifier corresponding to a specific mode of operation so that activation of a specific mode by said mode control means activates a corresponding mode amplifier.

21. The apparatus as claimed in claim 20 wherein the output of each of said mode amplifiers is controlled by mode amplifier gain control means.

22. The apparatus as claimed in claim 21 wherein said mode amplifier gain control means comprises first and second potentiometer means, said first potentiometer means controlling the gain of all mode amplifiers of one command group, and said second potentiometer means controlling the gain of all mode amplifiers of the other command group.

23. The apparatus of claim 12 wherein said output isolation means comprises a transformer having a primary winding with first and second side taps, and having a secondary winding with a pair of side taps and a center tap, a D.C. voltage source, said first side tap of the primary winding of said transformer being coupled to the output of said amplifier means, said second side tap of the primary winding of said transformer being coupled to said D.C. voltage source, and the side taps and center tap of the secondary winding of said transformer being coupled through first, second, and third capacitors, respectively, to output terminals for monopolar, ground and bipolar electrosurgical electrode connection.

24. The apparatus of claim 19 wherein said voltage-controlled main amplifier comprises an input stage, a gain-control stage, a driver stage, and an output stage, the output of said driver stage being coupled through an isolation transformer to the input of said output stage.

25. The apparatus of claim 12 including means for selectively amplifying a pulse of each of said output pulse groups to achieve a ratio of peak power to RMS power greater than 19:1 for the coagulate command group.

26. The apparatus of claim 25 wherein said means for selectively amplifying the pulse of each of said output pulse groups is coupled to said amplifier means.

27. A multiple-mode electrosurgical generator for producing a plurality of modes of tissue destruction by electrosurgery, comprising high-frequency oscillator means; means for activating said high-frequency oscillator means; selection means for selecting the mode of tissue destruction; variable frequency divider means, the output of said high-frequency oscillator means being coupled to said variable frequency divider means, said variable frequency divider means producing an interrupt signal as a function of the output of said high-frequency oscillator means and of the mode of operation indicated by said selection means; amplifier means for amplifying the output of said high-frequency oscillator means; interrupt means having a plurality of inputs, the inputs of said interrupt means being coupled to the output of said high-frequency oscillator means and said variable frequency divider means, respectively, the output of said interrupt means being coupled to the input of said amplifier means, said interrupt means interrupting the output of said high-frequency oscillator means as a function of said interrupt signal to form output pulse groups of the output of said high-frequency oscillator means; and output isolation means coupled to the output of said amplifier means, said output isolation means providing isolated bipolar and monopolar electrosurgical voltage.

28. A multiple-mode electrosurgical generator for producing a plurality of modes of tissue transformation by electrosurgery, comprising high-frequency oscillator means adapted to produce output pulses of constant frequency, interrupt means for interrupting said output pulses to produce a series of output pulse groups, selection means for varying the number of said output pulses in each of said output pulse groups to produce tissue transformation corresponding to the mode selected, means for selectively amplifying an ionization pulse among said output pulses of each of said output pulse groups to achieve a ratio of peak power to RMS power of at least 10:1 in said ionization pulse, and output amplifier means for applying said output pulse groups to an electrosurgical electrode.

29. A multiple-mode electrosurgical generator as claimed in claim 28 wherein said selection means is adapted to select a pure cut mode with said ionization pulse having a ratio of peak power to RMS power of at least 10:1.

30. A multiple-mode electrosurgical generator as claimed in claim 28 wherein said selection means is adapted to select a blend mode with said ionization pulse having a ratio of peak power to RMS power of at least 11:1.

31. A multiple-mode electrosurgical generator as claimed in claim 28 wherein said selection means is adapted to select a dessicate mode with said ionization pulse having a ratio of peak power to RMS power of at least 10:1.

32. A multiple-mode electrosurgical generator as claimed in claim 28 wherein said selection means is adapted to select a fulgurate mode with said ionization pulse having a ratio of peak power to RMS power of at least 20:1.

* * * * *